US012714607B2

(12) United States Patent
Cohade et al.

(10) Patent No.: US 12,714,607 B2
(45) Date of Patent: Aug. 25, 2026

(54) COMPRESSION BANDAGE WITH OPTIMIZED SURFACE

(71) Applicant: Urgo Recherche Innovation Et Developpement, Chenôve (FR)

(72) Inventors: Céline Cohade, Saint-Jean-Bonnefonds (FR); David Grange, Bellegarde-en-Forez (FR); Serge Lecomte, Dijon (FR); Magali Roblot, Perrigny-les-Dijon (FR)

(73) Assignee: Urgo Recherche Innovation Et Developpement, Chenôve (FR)

( * ) Notice: Subject to any disclaimer, the term of this patent is extended or adjusted under 35 U.S.C. 154(b) by 728 days.

(21) Appl. No.: 17/636,611

(22) PCT Filed: Aug. 19, 2020

(86) PCT No.: PCT/FR2020/051485
§ 371 (c)(1),
(2) Date: Feb. 18, 2022

(87) PCT Pub. No.: WO2021/032931
PCT Pub. Date: Feb. 25, 2021

(65) Prior Publication Data

US 2022/0296428 A1 Sep. 22, 2022

(30) Foreign Application Priority Data

Aug. 22, 2019 (FR) ....................................... 1909345

(51) Int. Cl.
*A61F 13/02* (2024.01)
*D04B 21/18* (2006.01)

(52) U.S. Cl.
CPC ...... *A61F 13/0273* (2013.01); *A61F 13/0269* (2013.01); *D04B 21/18* (2013.01);
(Continued)

(58) Field of Classification Search
CPC .... A61F 13/00; A61F 13/01; A61F 13/01034; A61F 13/01029; A61F 13/01017;
(Continued)

(56) References Cited

U.S. PATENT DOCUMENTS 5,385,036 A 1/1995 Spillane et al.

FOREIGN PATENT DOCUMENTS

AU 2016360847 A1 * 6/2018 ............. D04B 21/18
CN 101624776 A 1/2010
(Continued)

OTHER PUBLICATIONS

WO2005038112A1 machine translation (Year: 2005).*
(Continued)

*Primary Examiner* — Caitlin A Carreiro
(74) *Attorney, Agent, or Firm* — Lippes Mathias LLP

(57) ABSTRACT

A compression bandage formed by a knit obtained by warp stitch technology, based on synthetic yarns which is made up of two textile surfaces whose textile structure is identical or different connected to each other by spacer yarns. Each textile surface has elastic yarns and the spacer yarn being a monofilament. The knit has a longitudinal elongation measured according to standard EN 14704-1 of between 30 and 160%. The textile surface which comes into contact with the skin has synthetic multifilament yarns, the filaments of which have a count of between 1.2 and 5 dtex and the number of filaments is between 15 and 150, and a dynamic coefficient of friction measured according to standard EN ISO 8295 greater than or equal to 0.25 and less than or equal to 1.2.

13 Claims, 2 Drawing Sheets

(52) U.S. Cl.
CPC .................. *D10B 2403/021* (2013.01); *D10B 2403/0311* (2013.01); *D10B 2509/028* (2013.01)

(58) Field of Classification Search
CPC ............ A61F 13/01008; A61F 13/0273; A61F 13/0269; A61F 13/08; A61F 13/00004; A61F 13/00008; A61F 13/00021; A61F 2013/00119; A61F 2013/00238; D04B 21/18; D10B 2403/021; D10B 2403/0311; D10B 2509/028
USPC .................................. 602/41, 44, 53, 75, 76
See application file for complete search history.

(56) References Cited

FOREIGN PATENT DOCUMENTS

| | | | | | |
|---|---|---|---|---|---|
| CN | 106470571 A | | 3/2017 | | |
| CN | 106983202 A | * | 7/2017 | | A63B 71/145 |
| CN | 108603316 A | | 9/2018 | | |
| EP | 0456917 A1 | * | 11/1991 | | C08L 75/04 |
| EP | 1052319 A1 | | 11/2000 | | |
| FR | 3044217 A1 | * | 6/2017 | | D04B 21/18 |
| WO | WO-9516416 A1 | * | 6/1995 | | D04B 21/18 |
| WO | WO-2005038112 A1 | * | 4/2005 | | D03D 1/04 |
| WO | WO-2006032096 A1 | * | 3/2006 | | A41D 13/0015 |
| WO | WO 2007/113340 A1 | | 10/2007 | | |
| WO | WO 2014/033418 A1 | | 3/2014 | | |
| WO | WO-2017089731 A1 | * | 6/2017 | | D04B 21/18 |

OTHER PUBLICATIONS

EP 0456917 A1 machine translation (Year: 1991).*
FR 3044217 A1 machine translation of claims (Year: 2017).*
FR 3044217 A1 machine translation of description (Year: 2017).*
Machine translation of CN 106983202 A (Year: 2017).*
French Search Report of FR 1909345, Apr. 20, 2020, 7 pages.
International Search Report of International Application No. PCT/FR2020/051485 dated Nov. 26, 2020 (English Translation), 2 pages.
International Preliminary Report on Patentability of International Application No. PCT/FR2020/051485 dated Feb. 17, 2022 (and English Translation), 13 pages.

* cited by examiner

[Fig. 1]
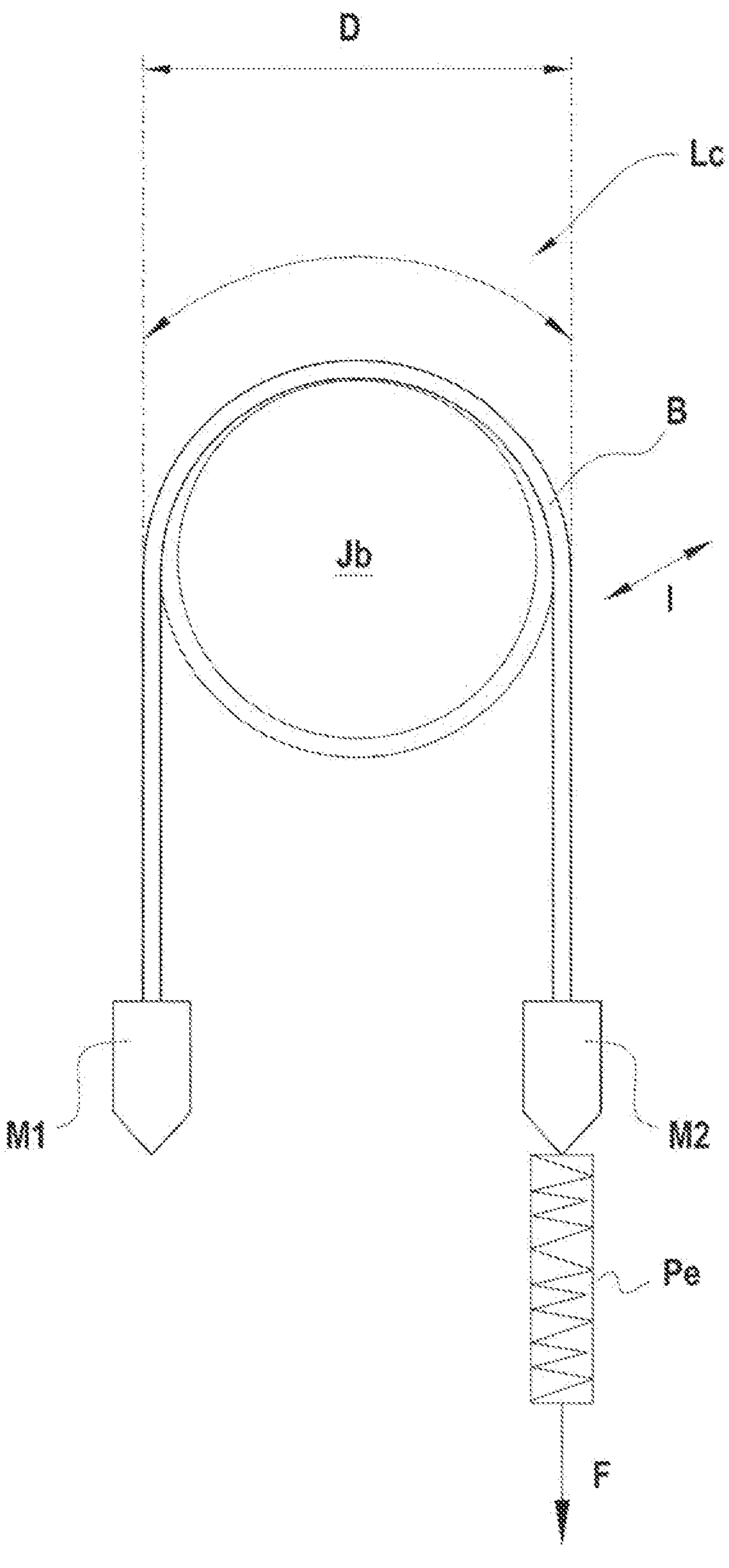

[Fig. 2]
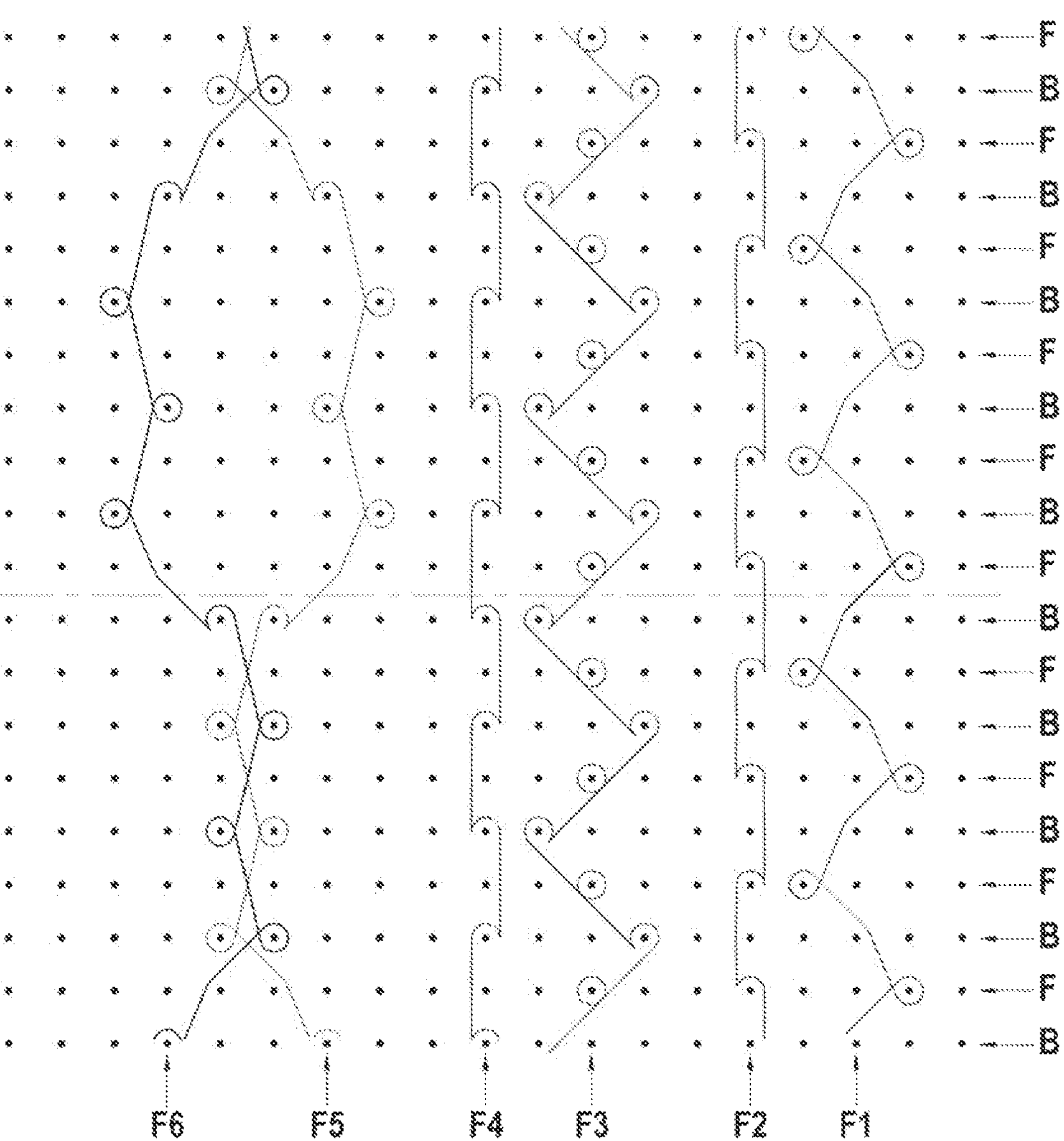

COMPRESSION BANDAGE WITH OPTIMIZED SURFACE

BACKGROUND OF THE DISCLOSURE

The present invention relates to a compression bandage, which is a 3D knit obtained according to the warp stitch technology, with no latex or adhesive, which does not loosen, allowing it to maintain its therapeutic effectiveness, and whose surface in contact with the skin has been modified to optimize its lack of slippage over time.

STATE OF THE ART

A compression bandage is caused to slip by three main factors. The quality of the application, the lateral slippage of the turns on each other and the ability of the bandage to resist slipping on the skin.

Patent application WO 2017/089731 describes characteristics that a 3D knit must have, used as a compression bandage, to combine therapeutic efficacy and durability without adding latex or adhesive to the bandage.

Thus, the ability to prevent the turn-on-turn slippage by means of a yield shear stress greater than or equal to 2800 Pa and securing the final fastening of the bandage at the end of the application make it possible to obtain products which fulfill these specifications.

But these bandages need to be improved further, especially on two points.

The first relates to the large-scale industrial manufacture of such 3D knits because bandages are obtained that do not fulfill this yield shear stress characteristic and therefore will loosen and slip during use.

Indeed, from the industrial viewpoint, bandages of a defined width, for example 10 cm are not produced, but rather sheets of 3D knits several metres wide and long are produced which are then cut into coils of defined widths and finally finished bandages usually 8 or 10 cm wide and about 3 to 3.5 meters in length. When manufacturing such sheets and performing these cutting operations, such surfaces have a substantial variability of the 3D knit and, in particular, bandages are obtained whose yield shear stress value is below or near the limit value.

The second is independent of the bandage itself; it is the friction of an article of clothing, such as pants, on the bandage when it is applied on a patient. This phenomenon especially appears when the space between the bandage and the pants is tight during movement.

Individuals vary widely in the morphology of the legs, which can be thin, thick, muscular, fatty, bony, or tapered, with little variation in diameter between the calf and ankle or curvy with prominent calves.

This cause of slippage is mainly observed in patients with curvy legs and prominent calves. This type of morphology in the context of treating leg ulcers or lymphoedema is rare because oedema is often present and the lack of physical activity due to the presence of the wound leads to patients with legs that are homogenous in diameter and/or not well muscled.

This type of leg morphology can be illustrated by the ratio between the point of the calf at its maximum circumference and the point of the ankle at its minimum circumference. When this ratio is greater than approximately 1.6, the slippage risk of the bandage increases.

When a movement is repeated quickly and very often, for example during walking, a slight drop of the bandage is observed at the end of several hours due to this friction. However, in the case of someone with a very curvy calf, once the maximum circumference of the calf is surpassed, since the bandage is still held in place because of the absence of turn-on-turn slippage, it loosens and eventually slips. Thus, the greater the calf diameter, the higher the risk of pant friction will be during movement.

Yet a patient generally wishes to conceal the presence of the bandage and wears pants nearly routinely. To remedy this problem of friction, patients sometimes cover the bandage with a high sock or stocking to avoid contact with the pants. But this solution is often poorly accepted since it adds an additional layer, increasing the heat experienced by the patient.

To remedy these problems and obtain a more universal product, which makes it possible to oppose pant friction and to avoid having to discard large quantities of bands at the end of production with a too low yield shear stress, the Applicant has attempted to optimize these 3D knits.

SUMMARY OF THE DISCLOSURE

In order to respond to these issues, the Applicant first tried to modify the surface state of the side coming into contact with the skin to increase the yield shear stress of these knits and, at the same time, the clinging character of the side coming into contact with the skin. The objective is to make it rougher, to increase friction with the other side, but also more clinging to the skin.

Various techniques are known to increase the roughness or the clinging character of the face of a textile product. For example, the use of yarns made of materials with a relatively high clinging character, such as silicone yarns, to adhere to the skin better. Another alternative is the creation of loops, by working on the textile construction, which protrude from the surface and lead to a rougher surface in contact with the skin and here would also increase friction with the other side and therefore the yield shear stress. However, these solutions complicate 3D knitting because other properties of the bandage are changed at the same time which are indispensable for its proper functioning and significantly increase the production cost, which is unacceptable. The difficultly also resides in the fact that, on the contrary, we seek to obtain a side in contact with the skin that has the softest feel possible because patient skin is often fragile or damaged, especially in the area where the bandage will be applied.

Contrary to what would seem logical and expected, the Applicant has found that it is advantageous to decrease the roughness of the side of the knit in contact with the skin by physical treatment to fulfill the complex specifications. Bandages thus treated, although they have yield shear stresses much lower than 2800 Pa and have a surface in contact with the skin softer than those of 3D knits described previously and therefore less clinging, surprisingly, do not exhibit tum-on-turn slippage nor slippage over time.

After thorough study of this unexpected situation, the Applicant determined what characteristics the treated surface should have to obtain such properties.

Greater leeway is thus obtained during industrial manufacture of the bandages, because the yield shear stress can be overcome and the bandages are also more effective and better accepted by the patient because the side coming into contact with the skin is softer.

The present invention therefore relates to a compression bandage that has the form of a knit obtained by warp stitch technology, based on synthetic yarns which is made up of two textile surfaces whose textile structure is identical or different connected to each other by a spacer yarn, each textile surface comprising elastic yarns and the spacer yarn is a monofilament, said knit has a longitudinal elongation measured according to standard EN 14704-1 of between 30 and 160%, characterized in that the textile surface coming into contact with the skin has synthetic multifilament yarns, the filaments of which have a count of between 1.2 and 5 dtex and the number of filaments of each multifilament yarn is between 15 and 150, and the textile surface coming into contact with the skin has a dynamic coefficient of friction measured according to standard EN ISO 8295 greater than or equal to 0.25 and less than or equal to 1.2, or for example greater than or equal to 0.25 and less than or equal to 0.5. The textile surface coming into contact with the skin is typically a physically-treated surface, for example a seeded surface.

Tests described below have shown that a bandage possessing such characteristics ensures that the turns do not slip on one another and also promotes its clinging character and is able to oppose slipping induced by pant friction.

According to the present invention, the 3D knit can be single use or reusable and therefore washable.

In order to favor precise application by the caregiver, the compression bandage may be provided with calibration means. These calibration means can be visual, such as, for example, by a collection of pictograms, regularly spaced and printed on the bandage or performed using a calibration system. Information on recommended application elongations can be supplied with the calibration tool. Calibration can also be performed by the caregiver in the form of a stencil. This type of stencil or the explanations necessary to fabricate it can be incorporated in the bandage packaging. A kit comprising several bandages of different constitutions, different widths, different lengths and/or endowed with different calibrations to apply specific pressures can also be used.

The kit can also comprise one or more wound dressings intended to be positioned on the wound before positioning the bandage.

In order to make handling easier during application, a knit is chosen which has a longitudinal elongation such as defined hi standard EN 14704-1 which is comprised between 40 and 160% or, more precisely, between 65 and 120% or, even more precisely, between 70 and 95%.

The knit has a thickness, for example, comprised between 1 and 2 mm, or more precisely between 1 and 1.5 mm.

The knit has a grammage, for example, comprised from 160 to 370 g/m$^2$, or more precisely from 180 to 300 g/m$^2$, or even more precisely from 200 to 250 g/m$^2$.

The knit has a space between the 2 textile sides comprised between 0.4 and 1.5 mm, or more precisely between 0.5 and 1.1 mm.

These grammage and thickness properties make the compression bandage easier to use with shoes. The compression bandage can thus also be more easily used with wadding if necessary. They also make it possible to reduce the risks of pant friction because the bandage is very thin.

The two textile surfaces of the knit can have identical or different textile structures. These textile structures can be solid or openwork.

Openwork textile structures, called openwork knits and designated in the present application by the term net, are well known to those skilled in the art. An openwork knit is a knit that has regular or irregular holes in its textile structure. These holes are obtained when, in the textile structure, one or more stitches in a column are not connected to the stitches in the neighboring column when knitting, typically by acting on the stitch pattern and/or on the threading.

According to one aspect of the present invention, the knit has two textile surfaces whose structure is different and, in particular, one textile surface which has an openwork textile structure called net side and a textile surface that has a solid side textile structure. The presence of a net side improves the breathability of the bandage. Such a net side is typically positioned in contact with a user's skin.

According to one particular embodiment, said knit has a side which has a textile structure of the charmeuse, single cord lap fabric or single tricot type with open or closed loops, atlas under one or more rows, or pillar stitch with open or closed loops, or alternating closed and open loops. This side is opposite the side designed to be brought into contact with the skin, which has a textile structure which is a net with the same type or a different type of textile but openwork.

In order to facilitate the passage of the heel and to avoid bandage constriction during application, 3D knits can be used which have a transverse elongation greater than 110% as measured according to method A, Section 9.2 of standard EN 14704-1, or for example comprised between 110% and 200%, or alternatively comprised between 120% and 180%.

Knits according to the invention are made, for example, using yarns commonly employed for making textile products, in particular knits. These yarns are synthetic, for example. These yarns are divided into two major categories: elastic yarns and thermoplastic yarns.

Elastic yarns include, for example, yarns based on polyurethane fibres such as elastane yarns marketed under the name LYCRA, elastodiene-based yarns or yarns based on triblock polymers (styrene-ethylene-butylene-styrene).

Thermoplastic yarns include yarns made up of synthetic materials which are not elastomers, such as, for example, polyester, polyamide, polypropylene or polybutylene terephthalate (PBT).

All these thermoplastic yarns can optionally be covered or textured.

The two textile surfaces of the 3D knit are created, for example, from elastic yarns and thermoplastic yarns. These yarns can be monofilaments or multifilaments. These textile surfaces can be made from identical or different yarns. The two surfaces will typically comprise similar elastic yarns.

The elastic yarns present on these textile surfaces have, for example, titres of around 40 to 80 dtex and the thermoplastic yarns have titres from 40 to 90 dtex.

The side coming into contact with the skin must contain thermoplastic yarns which are synthetic multifilaments. In order to obtain the right dynamic coefficient of friction after mechanical treatment, these multifilaments have filaments whose titre is comprised between 1.2 and 5 dtex and the number of filaments is comprised between 15 and 150.

These yarns are, for example, of polyamide, polyester or polypropylene. They can have a titre comprised between 25 and 200 dtex. In the context of the present invention, typically multifilament polyamide yarns are used which have a titre comprised between 40 and 90 dtex.

This side does not contain non-synthetic yarns such as, for example, cotton or viscose because these natural yarns are not resistant to the physical treatment.

On the side coming into contact with the skin, a quantity of multifilament thermoplastic yarns are used of around 15 to 40% by mass percentage relative to the total weight of the 3D knit and, for example, around 20 to 25%. The proportion of complementary yarns are elastic yarns.

If it is desirable to transfer moisture from the knit to the outside, non-synthetic yarns can be used on the side that does not come into contact with the skin.

For example, elastane yarns are used for the elastic yarns and polyamide or polyester yarns are used for the thermoplastic yarns.

The spacer yarns are typically monofilament thermoplastic yarns such as, for example, polyester, polypropylene or polyamide yarns.

According to one example, the spacer yarns are polyester or polyamide yarns that have a titre comprised, for example, between 20 and 80 dtex, or even between 40 and 70 dtex, or even more precisely, a polyester monofilament that has a titre between 44 and 55 dtex.

To perform the 3D knitting, a single bar can be used, for example, to knit the spacer yarn that binds the 2 textile surfaces.

The invention also concerns a kit comprising one or more compression bandages such as previously defined and one or more wound dressings designed to be positioned on a wound prior to one of the compression bandages.

The physical treatment of the surface coming into contact with the skin will be performed in a later step after knitting. The objective is to modify the surface state by altering the multifilaments. Physical treatments can include, for example, napping, brushing or sueding. In the context of the invention, sueding is typically used. This operation, well known in the clothing field, consists of heat-freezing the textile structure at a temperature of around 190° C. and then passing the textile one or more times under a roll of emery cloth. Obviously, any technical operation that makes it possible to obtain a surface coming into contact with the skin exhibiting the right characteristics can be employed.

These surface treatment processes of a textile material are commonly used.

However, to the Applicant's knowledge, no one has studied and assessed the impact of such a treatment to promote the absence of turn-on-turn slippage or the or the or the effect that is described as clinging to the skin.

Document EP 1052319 describes a 3D knit usable in orthopedic devices that surround a joint, for example, as illustrated in FIG. 7 of document EP 1052319, but never a compression bandage for which two layers of 3D knit are superimposed on top of each other to bandage the leg. The problem of turn-on-turn slippage is therefore not posed in this document.

The 3D knits developed in the context of the present disclosure are very different from existing 3D knits and especially those described in document EP 1052319 mentioned previously because the surface of known 3D knits catches with the hooks of a Velcro® type device, as opposed to the surface of 3D knits developed in the context of the present application which, after treatment, no longer catch with said hooks.

In the context of the present invention, due to this absence of catching of hooks, only the surface coming into contact with the skin is treated since, at the end of wrapping, the bandage is typically fastened onto these last two turns by means of such a device with hooks. In addition, the side opposite the one coming into contact with the skin is the on which the calibration is typically printed to facilitation applying the bandage and it may therefore be advantageous not to treat this surface so as not to alter the printing.

The surface state of treated 3D knits is therefore completely different from that sought in EP 1052319.

The microscopic observation of treated surfaces of 3D knits according to the invention shows that all or part of the fibres of the multifilaments are disorderly, disunited, threadbare, have rough spots, are less smooth and cut compared to the 3D knit before treatment, which explains the lack of catching with hooks.

This surface state of the treated side no doubt also explains why the yield shear stress value is significantly reduced relative to the examples of application WO 2017/089731. But in an unexplained way this nevertheless leads to a high-performing product in terms of preventing turn-on-turn slippage.

It is also seen, as illustrated by the tests described below, that the resistance to slippage on the skin is optimized.

But microscopic observation of the treated surface does not allow determining a number or shape of unstructured filaments which are essential to quantify this absence of turn-on-turn slippage and clinging to the skin of the bandage.

In the context of the present disclosure, we therefore sought to characterize the general surface state of such bandages.

In light of this, the Applicant studied the dynamic coefficient of friction of the side coming into contact with the skin which has been treated.

The dynamic coefficient of friction characterizes the aptitude of a surface to slip on itself or another surface. The measurement for this parameter, commonly used in the field of films, is described in standard EN ISO 8295.

Application WO 2014/033418 suggests the use of this standard to measure the bond between 2 sides of a compression bandage. But in this case, a physical clinging rather than friction is observed between the two sides because the loops present on the surface intertwine with each other. This leads to dynamic coefficient of friction values greater than 3. But in the context of the present invention, there is no physical clinging between the 2 sides of the same material as in WO 2014/033418. The term cling here illustrates only a friction between the skin and the side of the knit coming into contact with the skin.

The main difficulty resides here in the fact such a coefficient is measured between the skin and the side of a 3D knit that has substantial variability. Yet, the skin is particularly difficult to characterize and it is difficult to define an equivalent material.

It is therefore vital to find a reference material that can simulate the skin and be discriminating among 3D knits regarding the characterization of their surface state.

To the Applicant's knowledge, there is no method to measure cling to the skin of a bandage in vivo or in vitro. The development of a skin model is very complex and there is currently no model representative of the skin to assess this property. Moreover, there are a multitude of skins having distinct properties, especially color, presence of hair, or being oily, dry or damaged.

Finally, to be more representative, it is necessary to be under the conditions of use of the bandage which is applied stretched out and leads to a balance of force between the pressure applied and the force of friction between the bandage and the skin.

In order to be more realistic and to find a reference material, the Applicant developed a test to assess the friction of a bandage on the skin under conditions which Illustrate the conditions of the use applied stretched out.

This test is described in reference to FIG. 1, in which is schematically shown the leg Jb of a patient by a circle around which a bandage B has just been applied.

Assessing the friction illustrates the resistance that the skin and the bandage in contact with one another oppose to slippage. The minimum friction force that must be overcome to trigger the start of slippage will be determined. The coefficient of friction is the ratio between two forces that are applied here: the force necessary to overcome the movement that one measures and the force of contact imposed by the stretched out bandage which corresponds to the pressure applied by two weights at equilibrium on the surface of the bandage in contact with the skin Sc (Sc=Lc*I), where Lc is the length of the bandage in contact with the skin and I is the width of the bandage).

The test is described as follows:

The tester is seated and positions their heel on a support, for example a chair, so as to have the leg straight along the horizontal axis.

A bandage sample is cut longitudinally in a width of 5 cm and a length of 50 cm.

The bandage sample is applied on the side opposite the calf at the largest circumference of the calf so as to have equivalent lengths of bandage on each side of the leg as illustrated in FIG. 1.

At each end on the width of the bandage, two weights M1 and M2 of 500 g are fastened as illustrated in FIG. 1 to exert a pressure force of the same order of magnitude (around 35 mmHg here) as the pressure exerted by the bandage on the leg when this bandage is stretched out. The side of the knit in contact with the leg is the side which will be in contact with the skin in the normal use of the product. The bandage-skin friction forces hold the two weights immobile. A load cell Pe is positioned at one of the ends of the bandage below the weight.

The objective of the test is to pull on the load cell side manually, lightly and progressively until a slipping movement of the bandage is induced and to record the force F which makes it possible to set everything in motion, i.e., the bandage and the weights. The force is measured directly with a conventional load cell calibrated and equipped with an index to measure this force.

Because the values of weights M1 and M2 (which are identical and equal to M) and the force F are known, by calculation with the formula Math. 1 below (assuming that the leg is cylindrical and that the diameter D of the leg and the contact length Lc are identical) the coefficient of friction μ of the bandage on the skin can be estimated.

$$\mu = \frac{F}{2 \times M \times g + F} \times \frac{2}{\pi} \quad \text{[Math. 1]}$$

Where F is expressed in Newtons, M in kg and g=9.81 m/s/s. The patient's leg is considered here as a perfect cylinder; this approximation has little impact on the result.

The mean value, on the basis of this test, of the coefficient of friction of the 3D knits according to the invention on the skin is 0.28.

But to select or characterize the bandages at the end of production, an in vivo test is unsuitable. To find a reference material that can be used in the in vitro test described in standard EN ISO 8295 in a second step, the Applicant reproduced this test but by first positioning a sample of reference material around the leg at the place where the bandage will be applied, which will surround the leg on the surface which will be covered by the bandage during the test, fastened using a double-sided adhesive, on which the bandage sample will be positioned. The test then leads to the measurement of the coefficient of friction of the bandage on the material.

Using this approach, he sought to find a material that would be usable in an in vitro test to characterize the surface state of bandages and be able, if necessary, to select the bandages that exhibit the best surface state.

The Applicant then tested various materials to try to find one that had the same coefficient of friction result. He did not find any, but he determined a more discriminating material on which the coefficient of friction gives a value of 0.19.

This material is nonwoven and based on high density polyethylene which has a grammage of 82 g/m$^2$ and a smooth side, on which the side of the 3D knit that comes into contact with the skin is placed during the test, marketed by the company DuPont de Nemours under the trade name "Tyvek®". This material is used as a sealing material on roofs and underlayment for exterior walls and partitions. Its reference is TYVEK® TOITURE 45.

He therefore chose this material as the reference material to implement the above-mentioned standard.

By means of the use as a reference material for this test, it is thus possible to characterize and quantify the surface state of the 3D knits and to obtain a discriminating value correlated with the absence of turn-on-turn slippage and the non-slippage of the bandage. It could thus be determined that the surface must have a dynamic coefficient of friction greater than or equal to 0.25 and less than or equal to 1.2.

Indeed, it was considered that for a dynamic coefficient of friction greater than 1.2, it is not friction between the two materials that is measured according to the standard EN ISO 8295 but rather a physical dinging between these two materials as in document WO 2014/033418.

In the context of the present disclosure, 3D knits are typically used which have a dynamic coefficient of friction comprised between 0.25 and 0.8 and, for example, between 0.3 and 0.5.

It was also determined that to obtain both a soft aspect but also sufficient clinging properties on the skin that lead to a surface that has this characteristic it is necessary for the multifilaments on the surface of the side coming into contact with the skin to also have specific characteristics.

These multifilaments must be synthetic because natural yarns are not resistant to the physical treatments. Appropriate multifilaments are those whose filaments have a titre comprised 1.2 and 5 dtex and the number of filaments is comprised between 15 and 150.

It actually seems that the destructuring of synthetic yarns based on multifilaments in such ranges of values makes it possible to obtain filaments on the surface of the bandage that are thin enough not to damage the skin but increase friction when the side in contact with the skin is treated, and long enough to promote friction between the turns.

The present invention therefore relates to bandages whose longitudinal elongation is comprised between 30% and 160%, which are 3D knits, obtained according to the warp stitch technology, with no latex or adhesive, whose spacer yarn is a monofilament, which have on their surface coming into contact with the skin synthetic multifilament yarns whose filaments have a titre comprised between 1.2 and 5 dtex and the number of filaments of each multifilament yarn is comprised between 15 and 150, said multifilament yarns being, for example, destructured by a mechanical operation so that the side (or textile surface) coming into contact with the skin has a dynamic coefficient of friction greater than or equal to 0.25 and less than or equal to 1.2, which do not slip for at least 48 hours and at best for 3 days or more.

Indeed, in the context of treating leg ulcers that have highly exuding wounds, these minimum times of 48 and 72 hours correspond to the usual times for changing the dressings which are placed under the compression bandages.

BRIEF DESCRIPTION OF THE DRAWINGS

The invention and its advantages will be better understood upon reading the detailed description made below of the different embodiments given by way of nonlimiting example.

FIG. 1 shows a schematic of a test device applied to a user's leg to assess the friction of a bandage on the skin.

FIG. 2 shows a diagram of a stitch structure for producing a knit according to the present disclosure.

DETAILED DESCRIPTION OF THE DISCLOSURE

An example of implementation of the invention is described below.

Step 1.

A knit sheet of approximately 40 cm wide is fabricated according to the invention on a 22 gauge warp stitch double needle bed raschel loom.

To create this sheet, 6 bars were used according to the stitch diagram shown in FIG. 2 with the following yarns and conditions:

Nature of the Yarns:

- F1: polyamide yarn sold by the RADICI company under the reference 78/18/1 dtex S Beige.
- F2: elastane yarn of 44 dtex sold by the ASAHI KASEI GROUP.
- F3: yarn which is a polyester monofilament of 55 dtex sold by the FILVA company.
- F4: elastane yarn of 44 dtex sold by the ASAHI KASEI GROUP.
- F5: polyamide 66 yarn sold by DEFIBER SA under the reference PA 66 1/44/34.
- F6: polyamide 66 yarn sold by DEFIBER SA under the reference PA 66 1/44/34.

Knitting Loom Settings

- F1: feed 2650 mm of yarn consumed for making 480 stitches, full threading,
- F2: feed 1170 mm of yarn consumed for making 480 stitches, 1 full/1 empty threading,
- F3: feed 3700 mm of yarn consumed for making 480 stitches, full threading,
- F4: feed 1270 mm of yarn consumed for making 480 stitches, 1 full/1 empty threading,
- F5: feed 2150 mm of yarn consumed for making 480 stitches, 3 full/1 empty threading,
- F6: feed 2150 mm of yarn consumed for making 480 stitches, 3 full/1 empty threading.

Stitch Diagram.

FIG. 2 shows the graph of an example of stitch structure for the creation of a knit according to a particular embodiment of the invention.

In this figure, the front edge is shown by reference F, and the rear edge by reference B. The stitch diagrams of the yarns F1 to F6 are then illustrated.

It is clearly understood that this example is purely illustrative and that it should not be interpreted in a limiting manner with regard to the scope of the invention.

The sheet thus created undergoes a cutting step to create bandages 10 cm wide.

Physical Treatment.

A 40-cm wide sheet obtained as in step 1 is then physically treated on its side coming into contact with the skin, for example by sueding. The surface coming into contact with the skin is typically a sueded surface.

During this step, the knit undergoes several treatment steps. It is first treated at 190° C. at a rate of 10 m/min than successively passed into contact with two emery grain rollers, the first with grains of 280 and the second of 400 followed by a final step of heating at 120° C. at the same rate as the first step.

The sheet thus treated undergoes a cutting step to create bandages 10 cm wide.

The following techniques have been used to assess the parameters of the bandages obtained.

Grammage Measurement.

The grammage is measured according to standard NF EN 12127. Five test pieces with an area of 1000 $cm^2$ are weighed (measure=+/−1%) with a balance with an accuracy of not more than 1 mg.

The weighing is performed at a temperature of 21° C.+/−2° C. and 60%+/−15% RH.

The final measurement is a mean of 5 test pieces.

Thickness Measurement.

The thickness is measured according to standard NF EN ISO 9073-2. A TESTWELL DM 100 micrometre is used. The application pressure is set at 0.5 kPa and the area of the steel disk is 2500 $mm^2$.

The final measurement is a mean of 3 test pieces of the bandage.

Measurement of the Space Between the Sides.

This measurement is performed as follows.

Using a KEYENCE digital microscope (100× or 200× lenses) the space between the two planes of the two textile surfaces is determined.

The middle plane of the 2 surfaces is embodied by a horizontal line estimated by the operator and the distance between the two lines is determined automatically by the software. The measurement is reproduced several times and the mean of the measurements obtained is taken.

Measurement of the Yield Shear Stress.

The measurements are performed using a DHR rheometer 2 sold by the company TA Instruments.

They are conducted at a temperature of 35° C. (so as to be close to the temperature of bandages in contact with skin) said temperature being regulated by a Peltier plate with which the rheometer is equipped.

Two disks of 25 mm diameter are cut from the 3D knit analyzed.

These two disks are respectively glued using a thin and rigid double side adhesive sold by the company PLASTO under the reference P753 onto the metal face of the moving plate and the Peltier plate of the rheometer. The two 3D knit disks are contacted, charmeuse structure side (also called single cord lap structure) on the net structure side, by applying a pressure of 5.3 kPa (i.e. the equivalent of 40 mmHg). The rheometer control program generates a stress gradient (torsional torque) which varies from 100 to 10,000 Pa in 600 seconds. The device records the first microdisplacement it detects which corresponds to the yield shear stress expressed in Pa.

The instrumental uncertainty of this measurement is considered to be plus or minus 6%.

The final measurement is the mean of the values obtained for 5 samples of the same 3D knit bandage.

Measurement of the Dynamic Coefficient of Friction.

The measurement of the dynamic coefficient of friction is based on the principal described in standard EN ISO 8295. It uses as a reference material the product sold by the DuPont de Nemours company under the name Tyvek® whose reference is TOITURE 45. This material is nonwoven and based on high density polyethylene which has a grammage of 82 g/m$^2$ and a smooth side, on which the side of the 3D knit that comes into contact with the skin is placed. It consists of measuring, by an electronic dynamometer, the force to move, on a large plate, a 200-g square steel pad of 63.5 mm in length and 63.5 mm in width, which is covered with the compression bandage with the side coming into contact with the skin outwards, which slides on the large plate which is also covered over its entire surface with Tyvek®, the smooth side outwards in the same way. The surface of the bandage coming into contact with the skin is therefore in contact with the smooth side of the Tyvek® and the pad is pulled at the speed of 100 mm/min by the dynamometer. The bandage and the Tyvek® are affixed to the steel pad and to the plate using double-sided adhesive. The pad is connected by a cable to the force sensor of the dynamometer. The measurement of the dynamic coefficient of friction is the ratio between the tractive force, expressed in Newtons, measured by the dynamometer and the weight of the pad, expressed in Newtons, or 1.96 N as defined in the standard. The measurement is done on three samples cut from the same bandage and the mean of these three measurements is taken.

Measurement of Longitudinal and Transverse Elongation.

This is based on the measurement of the longitudinal elongation of the bandage as defined in method A, Section 9.2 of standard EN 14704-1 when the bandage is subjected to a maximum tractive force of 5 N/cm.

The conditions for performing the measurements are as follows.

A test piece of the material to be tested of 100 mm wide and 150 to 200 mm long is cut and positioned without pre-stress in the jaws of an electronic dynamometer (for example a dynamometer marketed by the MTS Systems corporation) so as to have a width of 100 mm and a useful reference length of 100 mm. The dynamometer stretches the test piece at a rate of 100 mm/min up to a maximum force of 5 N/cm then the then the crosshead returns to its initial position at the same return rate of 100 mm/min. This cycle is conducted 5 times and the elongation obtained at the fifth cycle, expressed in percentage, is directly calculated by the device. The operation is repeated on 5 test pieces then the mean value is calculated, which defines the longitudinal elongation of the bandage.

The transverse elongation of the bandage is assessed according to the same protocol but by adjusting the dimensions of the test piece to the width of the bandage, which is 10 cm. A test piece of 60 mm long and 50 mm wide is therefore used.

The parameters of the bandage obtained are as follows.

Untreated bandage:

Grammage: 238 g/m$^2$

Thickness: 1.6 mm

Yield shear stress: 2947 Pa

Space between the sides: 0.88 mm

Longitudinal elongation according to standard EN 14704-1: 80%

Transverse elongation according to standard EN 14704-1: 144%

Dynamic coefficient of friction according to standard EN ISO 8295: 0.22.

Treated bandage:

Grammage: 202 g/m$^2$

Thickness: 1.2 mm

Yield shear stress: 2357 Pa

Space between the sides: 0.74 mm

Longitudinal elongation according to standard EN 14704-1: 84%

Transverse elongation according to standard EN 14704-1: 150%

Dynamic coefficient of friction according to standard EN ISO 8295: 0.34.

Using the following test for the 2 bandages above the durability of the bandage is checked.

Among the usual testers, the one with the highest number of bandages slipping during the tests was selected. He has very muscular and curvy calves, which results in a ratio between the point where the calf has its maximum circumference and the point where the ankle has its minimum circumference of around 1.7.

The operating procedure for this in-vivo test is as follows.

The bandage(s) are wrapped around the leg according to the recommendations described in the package leaflet for the URGO K2®, two-layer system, which comprises two separate bandages, a so-called KTECH bandage and a so-called KPRESS bandage.

As a reminder, this leaflet recommends the following application method:

1) hold the foot at 90°, toes up; apply KTECH at the base of the toes by making two anchoring turns, ensuring that the padded side is in direct contact with the skin and that the pressure indicator is located on the upper side of the bandage; continue by making a figure 8 around the ankle, without putting excessive tension on the foot and covering the heel well;
2) wrap up to the knee by making spirals and stretching the bandage appropriately: the pressure indicator printed on the bandages should form a circle; to achieve proper coverage, the pressure indicator should be just covered (50% coverage); finish 2 cm below the knee and cut the excess bandage;
3) apply KPRESS over KTECH using the same technique starting one finger above KTECH and finishing one finger below KTECH so that only KTECH is in direct contact with the skin; once applied, press gently on the bandage with your hands to ensure the system holds well.

It is understood that this last step 3) is not necessary if a second self-adhesive compression bandage is not used. In this case, the last turn is fastened to itself using the hooked part of a Velcro® fastener. However, one presses gently on the bandage again with the hands to ensure the compression system is held securely.

To test the compression bandages of the previous examples, their elongation on application was determined as indicated in patent application WO2017/089731, page 28, line 21 to page 29, line 13. Thus, in order to test the compression bandages according to the invention, the elongation on application of the bandage was determined according to the working pressure sought, of around 60 to 70 mmHg, for example using a tensile-rupture curve as defined in standard EN ISO 13934-1. According to the law of Laplace, the elongation to be applied corresponds to the pressure sought. The principle of this standard is as follows: A rectangular bandage is cut of sufficient width while fraying it if necessary to obtain a sample of final width of 50 mm. This sample is placed in the jaws of a dynamometer 200 mm apart. The tensile test proceeds until the sample is broken at a rate of 100 mm/min. The test is repeated in this way for 5 samples. The conditioning, hygrometry and temperature conditions are defined in standard EN ISO 13934-1.

To apply the bandage properly, the bandages were calibrated using a stencil as described in patent application WO 2007/113340 page 13, line 18 to page 14, line 6.

In this way, an elongation on application of 45% was determined and the corresponding calibration was performed.

Using a fine permanent marker, a vertical line is drawn over at least three turns, along the axis of the tibial crest, starting from the last turn wrapped. This mark is used as a reference to assess, using a ruler graduated in mm, the horizontal shift of the line at the end of the test duration. During movements, this line loses its rectilinear character and exhibits a staggered appearance that is increasingly evident as the turn-on-turn slippage increases. If the turn-on-turn slippage is very slight or nonexistent, the vertical line remains intact or varies very little mainly on the first turn which is located under the last turn wrapped.

This shift of the vertical line represents the loosening of the bandage and illustrates its potential slippage over time. The test lasts 6 hours. At the end of 6 hours, the shift of the vertical line is measured on the first 3 turns.

Using a fine permanent marker, a vertical line is drawn on the skin above the last turn wrapped. This mark is used as a reference to assess, using a ruler graduated in mm, the vertical shift between this line and the position on the leg of the last turn at the end of the test duration. If the deviation between the horizontal line and the last turn is, at the end of 6 hours, greater than 15 mm, it is considered that the bandage will slip completely before 24 hours.

During the 6 hours, the tester conducts a usual activity without specific exertion.

A first test is conducted in which the tester wears an untreated bandage on each leg.

The left leg has a circumference difference ratio of 38/22 or 1.73 and the left leg of 38/22.5 or 1.68.

At the end of 6 hours, a drop in the horizontal line of 17 mm is observed on the left leg as well as a shift between the first turn and the second of 6 mm and between the second and the third of 8 mm. On the right leg, a drop in the horizontal line of 2 mm is observed as well as a shift of 2 mm between the first turn and the second and no shift between the second and the third turn.

In the case of the right leg, we have the standard behavior of a bandage described in WO2017/089731 which has a yield shear stress greater than 2800 Pa, here 2947 Pa, and there is no significant turn-on-turn slippage or slippage along the leg.

Conversely, in the case of the left leg, at the end of 6 hours the bandage exhibits a shift of the horizontal line of 17 mm and turn-on-turn shifts that increase as you go down the leg. This illustrates the influence of pant friction in the case of a curvy calf. No doubt it is friction from the pants on the bandage that causes it to drop slightly over time. Once the maximum circumference of the calf is exceeded, the bandage begins to loosen as is illustrated by the turn-on-turn shift observed which will then lead to more substantial slippage of the bandage. This bandage will slip completely very quickly.

A second, similar test was conducted with the same tester but with a treated bandage on each leg this time.

In return, since these bandages are supposed to be better performing in terms of slippage and cling to the skin, the test conditions were made more demanding. Intense physical activity was introduced by adding 1 h 30 min of continuous treadmill walking after application and 30 additional minutes of walking at the end of 4 hours. Finally the tester wore conventional denim jeans, likely to increase friction, and the test lasted 7 hours.

At the end of 7 hours, no turn-on-turn shift was observed on either of the 2 legs as well as minimal vertical shifts of 0.3 mm on the right leg and 0.6 mm on the left leg.

These treated bandages therefore fulfill the target specifications even under the most unfavorable conditions.

The previous test illustrates the fact that a physically treated bandage, even if it has a yield shear stress well below 2800 Pa, 2357 Pa here, but a dynamic coefficient of friction greater than 0.25, 0.34 here, allows obtaining results with no turn-on-turn slippage and durability identical to those of a bandage which has a yield shear stress greater than 2800 Pa, 2937 Pa here.

The treatment that leads to a surface state, characterized by the measurement of the dynamic coefficient of friction greater than 0.25 therefore clearly makes it possible to overcome the limit of the yield shear stress value. Moreover, despite the more unfavorable test conditions and a longer duration, it is also observed that the treated bandage exhibits insignificant horizontal slippage. It therefore presents an improved friction on the skin relative to the untreated bandage. This is illustrated by the dynamic coefficient of friction value, which is 0.34, therefore greater than 0.25, versus 0.22 for the untreated bandage. Although these values seem close, these deviations are significant because small variations of properties are measured. Although the present invention has been described by referring to specific examples of embodiment, it is obvious that modifications and changes can be made without exceeding the general scope of the invention as defined by the claims. In particular, individual characteristics of the different embodiments illustrated/discussed can be combined into additional embodiments. Consequently, the description and the drawings should be considered in an illustrative rather than a restrictive sense.

It is also obvious that all the characteristics described with reference to a method can be transposed, alone or in combination, to a device, and conversely, all the characteristics described with reference to a device can be transposed, alone or in combination, to a method.

The invention claimed is:

1. A compression bandage configured for medical treatment of a user, said bandage having a form of a 3D knit obtained by warp stitch technology, with no latex or adhesive, based on synthetic yarns which is made up of two textile surfaces whose textile structure is identical or different connected to each other by spacer yarns, each of the two textile surfaces comprising elastic yarns and the spacer yarn being a monofilament, said 3D knit having a longitudinal elongation measured according to standard EN 14704-1 of between 30 and 160%, wherein a textile surface configured for coming into contact with human skin has synthetic multifilament yarns, the filaments of which have a count of between 1.2 and 5 dtex and the number of filaments of each multifilament yarn is between 15 and 150, wherein the textile surface configured for coming into contact with human skin has a quantity of multifilament yarns of around 15 to 40% by mass percentage relative to the total weight of said 3D knit and typically around 20 to 25%, and the textile surface configured for coming into contact with human skin has a physically treated surface wherein the textile surface configured for coming into contact with human skin is treated with a physical treatment selected from brushing or sueding such that the multifilament yarns on the physically treated surface include fibers that are disorderly, disunited, threadbare, have rough spots, are less smooth and are cut, as compared to an untreated surface, and wherein the physical treatment and resulting structure of the multifilament yarns provides a dynamic coefficient of friction measured according to standard EN ISO 8295 of greater than or equal to 0.25 and less than or equal to 1.2, to prevent turn-on-turn slippage.

2. The compression bandage according to claim 1, wherein said 3D knit has a grammage comprising between 160 and 370 g/m$^2$.

3. The compression bandage according to claim 2, wherein said 3D knit has a grammage comprising between 160 and 300 g/m$^2$.

4. The compression bandage according to claim 1, wherein the spacer yarn is a monofilament having a titre comprising between 20 and 80 dtex.

5. The compression bandage according to claim 1, wherein said 3D knit has a side which has a textile structure among the following list:

- charmeuse;
- single cord lap fabric with open or closed loops;
- atlas under one or more rows;
- pillar stitch with open or closed loops, or alternating closed and open loops, said side being opposite a side designed to be brought into contact with the human skin, which has a textile structure which is a net having an openwork textile structure.

6. The compression bandage according to claim 1, wherein said 3D knit has a thickness comprising between 1 and 2 mm.

7. The compression bandage according to claim 1, wherein said 3D knit has a space between the two textile surfaces comprising between 0.4 and 1.5 mm.

8. The compression bandage according to claim 1, wherein said 3D knit has a longitudinal elongation such as defined in standard EN 14704-1 comprising between 70 and 100%.

9. The compression bandage according to claim 1, wherein the elastic yarn has a titre comprising between 40 and 80 dtex.

10. The compression bandage according to claim 1, wherein the two textile surfaces comprise thermoplastic yarns having titres from 40 to 90 dtex.

11. The compression bandage according to claim 1, wherein a side configured for coming into contact with human skin has a dynamic coefficient of friction measured according to standard EN ISO 8295 greater than or equal to 0.25 and less than or equal to 0.5.

12. The compression bandage according to claim 1, wherein the textile surface configured for coming into contact with human skin is a sueded surface.

13. A kit comprising one or more compression bandages according to claim 1 and one or more wound dressings designed to be positioned on a wound prior to the compression bandage.

* * * * *